US011013722B2

(12) United States Patent
Takizawa et al.

(10) Patent No.: US 11,013,722 B2
(45) Date of Patent: *May 25, 2021

(54) THERAPEUTIC AGENT FOR DYSLIPIDEMIA

(71) Applicant: KOWA COMPANY, LTD., Nagoya (JP)

(72) Inventors: Toshiaki Takizawa, Higashimurayama (JP); Yasunobu Yoshinaka, Higashimurayama (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,050

(22) Filed: Feb. 11, 2019

(65) Prior Publication Data

US 2019/0167645 A1 Jun. 6, 2019

Related U.S. Application Data

(63) Continuation of application No. 15/904,922, filed on Feb. 26, 2018, now Pat. No. 10,258,609, which is a continuation of application No. 15/399,856, filed on Jan. 6, 2017, now Pat. No. 9,931,321, which is a continuation of application No. 14/429,449, filed as application No. PCT/JP2013/005756 on Sep. 27, 2013, now Pat. No. 9,572,798.

(30) Foreign Application Priority Data

Sep. 27, 2012 (JP) .................................. 2012-214635

(51) Int. Cl.
*A61K 31/423* (2006.01)
*A61K 31/397* (2006.01)
*A61K 45/06* (2006.01)

(52) U.S. Cl.
CPC .......... *A61K 31/423* (2013.01); *A61K 31/397* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2005/0101636 A1 | 5/2005 | Yamazaki et al. | |
| 2006/0189667 A1 | 8/2006 | Yamazaki et al. | |
| 2008/0255202 A1 | 10/2008 | Bischoff et al. | |
| 2010/0069433 A1 | 3/2010 | Takizawa et al. | |

FOREIGN PATENT DOCUMENTS

| | | |
|---|---|---|
| CA | 2535749 A1 | 3/2005 |
| CA | 2680407 A1 | 10/2008 |
| CN | 101627021 A | 1/2010 |
| EP | 1 661 890 A1 | 5/2006 |
| EP | 2141155 A1 | 1/2010 |
| WO | 02/058732 A2 | 8/2002 |
| WO | 03/043997 A1 | 5/2003 |
| WO | 2004/103997 A1 | 12/2004 |
| WO | 2005/009942 A1 | 2/2005 |
| WO | 2005/023777 A1 | 3/2005 |
| WO | 2005/097784 A1 | 10/2005 |
| WO | 2006/033891 A2 | 3/2006 |
| WO | 2006/049232 A1 | 5/2006 |
| WO | 2007/008529 A2 | 1/2007 |
| WO | 2007/008541 A2 | 1/2007 |
| WO | 2008/006043 A2 | 1/2008 |
| WO | 2008/033464 A2 | 3/2008 |
| WO | 2008/104875 A1 | 9/2008 |
| WO | 2008/120472 A1 | 10/2008 |
| WO | 2009/047240 A1 | 4/2009 |
| WO | 2009/080248 A1 | 7/2009 |

OTHER PUBLICATIONS

International Search Report dated Dec. 17, 2013, issued in corresponding application No. PCT/JP2013/005756.
Tanimoto, "Research and developmental strategy of anti-dyslipidemic agents" Folia Pharmacol. Jpn., 2007, pp. 267-270, vol. 129.
Schoonjans et al., "Role of the peroxisome proliferator-activated receptor (PPAR) in mediating the effects of fibrates and fatty acids on gene expression", Journal of Lipid Research, 1996, pp. 907-925, vol. 37.
Barbier et al., "Genomic and non-genomic interactions of PPAR? with xenobiotic-metabolizing enzymes" Trends in Endocrinology and Metabolism Sep. 2004, pp. 324-330, vol. 15, No. 7.
Farnier et al., "Efficacy and safety of the coadministration of ezetimibe with fenofibrate in patients with mixed hyperlipidaemia", European Heart Journal, 2005, pp. 897-905, vol. 26.
Farnier, "Pharmacotherapy of Mixed Hyperlipidemia with Ezetimibe-Fenofibrate Combination Therapy", Clinical Medicine: Therapeutics, 2009, pp. 1703-1713.
Takizawa et al., "K-877, a Highly Potent and Selective PPARA Agonist, Improves Dyslipidemia and Atherosclerosis in Experimental Animal Models", The 80th EAS Congress, May 2012, p. 787.
Takizawa et al., "(R)-K-13675, a highly potent and selective PPAR? agonist", J. Pharmacol. Sci., 2007, p. 244, "P3-088", vol. 103.
Yamazaki et al., "Ko Kassei katsu Ko Sentakuteki PPAR? Agonist no Sosei", Abstracts of 131st Annual Meeting of Pharmaceutical Society of Japan 1, 2011, p. 160, "S13-5".
Tanaka, "PPAR-? Agonist (Fibrate)", Life Style Medicine, 2008, pp. 65-71, vol. 2, No. 1.
Moon et al., "Ezetimibe and Fenofibrate Combination Therapy for Mized Hyperlipidemia" Drugs of Today, 2007, pp. 35-45, vol. 43, No. 1.

(Continued)

*Primary Examiner* — Craig D Ricci
(74) *Attorney, Agent, or Firm* — Westerman, Hattori, Daniels & Adrian, LLP

(57) ABSTRACT

The present invention addresses the problem of providing a pharmaceutical combination composition and drug combinations for the prevention and/or treatment of dyslipidemic conditions such as atherosclerosis, hypercholesterolemia, low HDL blood disease in mammals including humans. A pharmaceutical composition for the prevention and/or treatment of dyslipidemia, etc. which comprises (a) a compound represented by the general formula (1) (in the formula, each symbol is the same as defined in the specification) or a salt thereof or a solvate thereof and (b) a cholesterol absorption inhibitor.

8 Claims, 3 Drawing Sheets

(56) References Cited

OTHER PUBLICATIONS

Notification of Transmittal of Copies of Translation of the International Preliminary Report on Patentability (Form PCT/IB/338) of International Application No. PCT/JP2013/005756 dated Apr. 9, 2015 with Forms PCT/IB/373, PCT/ISA/237 and PCT/IB/326.
Office Action dated Jan. 3, 2016, issued in counterpart Chinese Application No. 201380047997.X.
Wang et al., "The research development of Ezetimibe as the cholesterol absorption inhibitory drug", China Pharmacy, vol. 20, No. 1, pp. 64-66.
Van Heek, Margaret et al., "Ezetimibe, a Potent Cholesterol Absorption Inhibitor, Normalizes Combined Dyslipidemia in Obese Hyperinsulinemic Hamsters", Diabetes, vol. 50, No. 6, pp. 1330-1335.
Extended Search Report dated Feb. 1, 2016, issued in counterpart European Application No. 13842381.9-1453.
McKenney, J.M., et al, "Safety and Efficacy of Long-Term Co-Administration of Fenofibrate and Ezetimibe in Patients With Mixed Hyperlipidemia", Journal of the American College of Cardiology, Nov. 2006, vol. 47, No. 8, pp. 1584-1587.
Syversenl, U. et al, "Different Skeletal Effects of the Peroxisome Proliferator Activated Receptor (PPAR) a Agonist Fenofibrate and the PPAR g Agonist Pioglitazone", BMC Endocrine Disorders, Mar. 2009, vol. 9, No. 10.
Office Action dated Oct. 12, 2016, issued in counterpart Taiwanese Application No. 102134981. (4 pages).
English Translation of Office Action dated Oct. 12, 2016, issued in counterpart Taiwanese Application No. 102134981.
Notice of Allowance dated Dec. 13, 2018, issued in U.S. Appl. No. 15/904,922.
Office Action dated Jun. 27, 2019, issued in Canadian Patent Application No. 2901650.

THERAPEUTIC AGENT FOR DYSLIPIDEMIA

CROSS-REFERENCE TO RELATED APPLICATION

This application is a continuation of U.S. application Ser. No. 15/904,922, filed on Feb. 26, 2018, which is a continuation of U.S. application Ser. No. 15/399,856, filed on Jan. 6, 2017, which is a continuation of U.S. application Ser. No. 14/429,449, filed on Mar. 19, 2015, which is a 371 of International Application No. PCT/JP2013/005756, filed on Sep. 27, 2013, which claims the benefit of priority from the prior Japanese Patent Application No. 2012-214635, filed on Sep. 27, 2012, the entire contents of which are incorporated herein by reference.

TECHNICAL FIELD

The present invention relates to a composition containing a compound (1) selectively activating an α-type (PPARα) of peroxisome proliferator-activated receptors (PPARs), and a cholesterol absorption inhibitor, which are intended to prevent and/or treat atherosclerosis, and a lipemia condition such as hypercholesterolemia; and a combination thereof.

BACKGROUND ART

In recent years, due to the westernization of diet, patients with hypercholesterolemia, hypertriglyceridemia, hypo-HDL cholesterolemia, and the like, which are in the category of a so-called lifestyle-related diseases, are in an increasing trend. Further, recently, patients with mixed or combined dyslipidemia, which has both hypercholesterolemia and hypertriglyceridemia, have been increased. Especially in patients with mixed dyslipidemia, LDL cholesterol (LDL-C) and triglyceride (TG) are increased, and HDL cholesterol (HDL-C) is decreased. Such a high TG and low HDL-C condition is also observed in patients with metabolic syndrome or diabetes. It has been proved that hyper LDL-cholesterolemia, hypo-HDL cholesterolemia, and hypertriglyceridemia are risk factors for coronary artery disease (CAD) or cerebral vascular disorder and the like. The importance of the management of dyslipidemia is described in "Guidelines for Preventing Arteriosclerotic Diseases, 2012 edition" released by Japan Atherosclerosis Society.

Dyslipidemia, in particular, hypercholesterolemia has already fallen into a disease area of high medical satisfaction with the advent of statins. However, from the results of a large number of large-scale clinical trials, it has been found that the further decrease of blood LDL cholesterol level leads to the prevention of coronary artery disease (the lower the better), and the more strict lipid control is recommended. There are a large number of patients who cannot reach the intended level of blood LDL-C only by the statins, and treatment with a combination of multiple agents has been required. On the other hand, for the hypertriglyceridemia, it has been indicated that fibrate-based agents more effectively reduce the level, and for the hypo-HDL cholesterolemia, research and development of CETP inhibitors, apo A-I increasing agents, and the like has been carried out. In particular, it has been expected that blood HDL-C increasing drugs are increasingly important in the future from the viewpoint of reverse transfer of cholesterol, and evolution suppression and regression of arteriosclerosis, (Non-Patent Document 1).

PPAR is one of the receptors that belong to a nuclear receptor family. It has been known of the presence of three subtypes (α,γ, and δ) in the receptor (Non-Patent Document 2). Among them, PPARα is mainly expressed in the liver, and when PPARα is activated, production of apo C-III is suppressed, and then lipoprotein lipase (LPL) is activated, as a result, fat is decomposed. As the PPARα agonist, unsaturated fatty acids; fibrate-based agents such as fenofibrate, bezafibrate, and gemfibrozil; and the like have been known (Non-Patent Document 3). Further, in recent years, a compound, which has a PPARα activating effect more strongly and selectively than the conventional fibrate-based agent does, has been reported (Patent Documents 1 to 10).

A cholesterol absorption inhibitor is an agent suppressing the absorption of dietary cholesterol from the small intestine. As to the factors to determine the blood cholesterol level, it is considered that contribution of de novo synthesized cholesterol in the liver is 70%, and contribution of the dietary cholesterol is 30%, therefore, the blood cholesterol levels can be reduced by the suppression of the absorption of dietary cholesterol from the small intestine, independently from the cholesterol synthesis inhibition by statins. As the cholesterol absorption inhibitor, for example, ezetimibe (Zetia (registered trademark)) has been known. The mechanism of its action was unknown for a long time, however, recently the mechanism that the absorption of cholesterol is suppressed by the inhibition of a cholesterol transporter (Niemann-Pick C1-like 1, NPC1-L1) expressed in the small intestinal epithelial cells has been elucidated. In addition to ezetimibe, multiple compounds having an inhibitory effect on the cholesterol transporter have been reported (Patent Documents 11 to 14).

Treatments with a combination of the above-described fibrate-based agent with ezetimibe have been investigated for patients with mixed dyslipidemia who have a feature that the blood LDL-C level and the blood TG level are increased, and the blood HDL-C level is decreased (Patent Document 15, and Non-Patent Documents 4 and 5). Meanwhile, it has not been known what kind of effect is exerted on the dyslipidemia if a compound (1) of the present invention is used in combination with ezetimibe.

CITATION LIST

Patent Document

Patent Document 1: WO 2005/023777
Patent Document 2: WO 2009/080248
Patent Document 3: WO 2009/047240
Patent Document 4: WO 2008/006043
Patent Document 5: WO 2006/049232
Patent Document 6: WO 2006/033891
Patent Document 7: WO 2005/009942
Patent Document 8: WO 2004/103997
Patent Document 9: WO 2005/097784
Patent Document 10: WO 2003/043997
Patent Document 11: WO 2007/008541
Patent Document 12: WO 2007/008529
Patent Document 13: WO 2008/033464
Patent Document 14: WO 2008/104875
Patent Document 15: WO 2002/058732

Non-Patent Document

Non-Patent Document 1: Folia Pharmacol. Jpn., 129, 267-270 (2007)
Non-Patent Document 2: J. Lipid Research 37, 907-925 (1996)
Non Patent Document 3: Trends in Endocrinology and Metabolism, 15(7), 324-330 (2004)
Non-Patent Document 4: European Heart Journal, 26, 897-905 (2005)
Non-Patent Document 5: Clinical Medicine: Therapeutics, 1, 1703-1713 (2009)

SUMMARY OF THE INVENTION

Problems to be Solved in the Invention

An object of the present invention is to provide a pharmaceutical combination composition and a drug combination for prevention and/or treatment of atherosclerosis, or a dyslipidemic condition such as hypercholesterolemia, and hypo-HDL cholesterolemia, and the like.

Means for Solving the Problems

As a result of intensive study, in view of the above circumstances, the present inventors found the fact that a strong blood HDL cholesterol increasing effect is exerted by a combination of a phenoxyacetic acid derivative represented by the following general formula (1) or a salt thereof, with ezetimibe that is a cholesterol absorption inhibitor, wherein the phenoxyacetic acid derivative represented by the following general formula (1) is disclosed in the Patent Document 1 to have a selective PPARα activating effect, not to be accompanied by weight gain or obesity in mammals including human beings, and to be useful as a prophylactic and/or therapeutic agent for dyslipidemia, arteriosclerosis, diabetes, diabetic complication (diabetic nephropathy and the like), inflammation, heart disease, and the like, and thus have completed the present invention.

That is, the present invention is to provide a pharmaceutical composition for preventing and/or treating dyslipidemia, including:
a) a compound represented by the following general formula (1):

[Chemical formula 1]

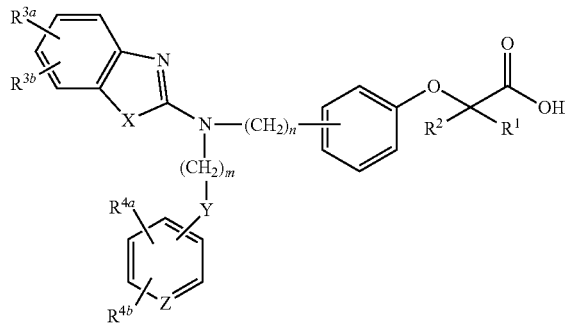

(1)

wherein $R^1$ and $R^2$, which may be identical or different, each represents a hydrogen atom, a methyl group, or an ethyl group; $R^{3a}$, $R^{3b}$, $R^{4a}$ and $R^{4b}$, which may be identical or different, each represents a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R^{3a}$ and $R^{3b}$, or $R^{4a}$ and $R^{4b}$ are joined to represent an alkylenedioxy group; X represents an oxygen atom, a sulfur atom, or N- $R^5$ (wherein $R^5$ represents a hydrogen atom, a $C_{1-4}$ alkyl group, a $C_{1-4}$ alkylsulfonyl group, or a $C_{1-4}$ alkyloxycarbonyl group); Y represents an oxygen atom, a $S(O)_l$ group (wherein l represents 0, 1 or 2), a carbonyl group, a carbonylamino group, an aminocarbonyl group, a sulfonylamino group, an aminosulfonyl group, or an NH group; Z represents CH, or N; n represents a number from 1 to 6; and m represents a number from 2 to 6, or a salt thereof, or a solvate of the compound, or a solvate of the salt of the compound; and
b) a cholesterol absorption inhibitor.

In more detail, the present invention is to provide a pharmaceutical composition for preventing and/or treating mixed dyslipidemia, metabolic syndrome, dyslipidemia complicated by diabetes, hypo-HDL cholesterolemia, or hypertriglyceridemia, including: a) a compound represented by the general formula (1) or a salt thereof, or a solvate of the compound, or a solvate of the salt of the compound; and
b) a cholesterol absorption inhibitor.

The more detailed description of the present invention is as follows.
(1) A pharmaceutical composition for preventing and/or treating dyslipidemia, including: a compound represented by the general formula (1) or a salt thereof, or a solvate of the compound, or a solvate of the salt of the compound; and a cholesterol absorption inhibitor.
(2) The pharmaceutical composition according to (1), wherein the compound represented by the general formula (1) is (R)-2-[3-[[N-(benzoxazol-2-yl)-N-3-(4-methoxyphenoxy)propyl]aminomethyl]phenoxy]butyric acid.
(3) The pharmaceutical composition according to (1) or (2), wherein the cholesterol absorption inhibitor is ezetimibe.
(4) The pharmaceutical composition according to any one of (1) to (3), wherein the dyslipidemia is a disease selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia).
(5) The pharmaceutical composition according to any one of (1) to (4), wherein an amount ratio of the compound represented by the general formula (1) to the cholesterol absorption inhibitor is 1:200 to 3:1.
(6) A pharmaceutical composition for increasing HDL cholesterol (HDL-C), including: a compound represented by the general formula (1) or a salt thereof, or a solvate of the compound, or a solvate of the salt of the compound; and a cholesterol absorption inhibitor.
(7) The pharmaceutical composition according to (6), wherein the compound represented by the general formula (1) is (R)-2-[3-[[N-(benzoxazol-2-yl)-N-3-(4-methoxyphenoxy)propyl]aminomethyl]phenoxy]butyric acid.
(8) The pharmaceutical composition according to (6) or (7), wherein the cholesterol absorption inhibitor is ezetimibe.
(9) The pharmaceutical composition according to any one of (6) to (8), wherein a disease requiring increase of HDL cholesterol (HDL-C) is a disease selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia).

(10) The pharmaceutical composition according to any one of (6) to (9), wherein an amount ratio of the compound represented by the general formula (1) to the cholesterol absorption inhibitor is 1:200 to 3:1.

(11) A method for preventing and/or treating dyslipidemia in a subject, comprising: administering to a subject with dyslipidemia or a subject with a risk of dyslipidemia an effective amount of a pharmaceutical composition containing a compound represented by the general formula (1) or a salt thereof, or a solvate of the compound, or a solvate of the salt of the compound, and a cholesterol absorption inhibitor.

(12) The method for preventing and/or treating dyslipidemia in a subject according to (11), wherein the compound represented by the general formula (1) is (R)-2-[3-[[N-(benzoxazol-2-yl)-N-3-(4-methoxyphenoxy)propyl]aminomethyl]phenoxy]butyric acid.

(13) The method for preventing and/or treating dyslipidemia in a subject according to (11) or (12), wherein the cholesterol absorption inhibitor is ezetimibe.

(14) The method for preventing and/or treating dyslipidemia with a subject according to any one of (11) to (13), wherein the dyslipidemia is selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia).

(15) The method for preventing and/or treating dyslipidemia in a subject according to anyone of (11) to (14), wherein an amount ratio of the compound represented by the general formula (1) to the cholesterol absorption inhibitor in the pharmaceutical composition is 1:200 to 3:1.

(16) A method for increasing HDL cholesterol (HDL-C) in a subject, comprising: administering to a subject requiring increase of HDL cholesterol (HDL-C) an effective amount of a pharmaceutical composition containing a compound represented by the general formula (1) or a salt thereof, or a solvate of the compound, or a solvate of the salt of the compound, and a cholesterol absorption inhibitor.

(17) The method according to (16), wherein the compound represented by the general formula (1) is (R)-2-[3-[[N-(benzoxazol-2-yl)-N-3-(4-methoxyphenoxy)propyl]aminomethyl]phenoxy]butyric acid.

(18) The method according to (16) or (17), wherein the cholesterol absorption inhibitor is ezetimibe.

(19) The method according to any one of (16) to (18), wherein a disease in a subject requiring increase of HDL cholesterol (HDL-C) is selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia).

(20) The method according to any one of (16) to (19), wherein an amount ratio of the compound represented by the general formula (1) to the cholesterol absorption inhibitor in the pharmaceutical composition is 1:200 to 3:1.

(21) A compound represented by the general formula (1) or a salt thereof, or a solvate of the compound, or a solvate of the salt of the compound, for use as a pharmaceutical combination composition for preventing and/or treating dyslipidemia in combination with a cholesterol absorption inhibitor.

(22) The compound or a salt thereof, or a solvate of the compound, or a solvate of the salt of the compound for use according to (21), wherein the compound represented by the general formula (1) is (R)-2-[3-[[N-(benzoxazol-2-yl)-N-3-(4-methoxyphenoxy)propyl]aminomethyl]phenoxy]butyric acid.

(23) The compound or a salt thereof, or a solvate of the compound, or a solvate of the salt of the compound for use according to (21) or (22), wherein the cholesterol absorption inhibitor is ezetimibe.

(24) The compound or a salt thereof, or a solvate of the compound, or a solvate of the salt of the compound for use according to any one of (21) to (23), wherein the dyslipidemia is selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia).

(25) The compound or a salt thereof, or a solvate of the compound, or a solvate of the salt of the compound for use according to any one of (21) to (24), wherein an amount ratio of the compound represented by the general formula (1) to the cholesterol absorption inhibitor in the pharmaceutical composition is 1:200 to 3:1.

(26) A compound represented by the general formula (1) or a salt thereof, or a solvate of the compound, or a solvate of the salt of the compound, for use as a pharmaceutical combination composition for increasing HDL cholesterol (HDL-C) in combination with a cholesterol absorption inhibitor.

(27) The compound or a salt thereof, or a solvate of the compound, or a solvate of the salt of the compound for use according to (26), wherein the compound represented by the general formula (1) is (R)-2-[3-[[N-(benzoxazol-2-yl)-N-3-(4-methoxyphenoxy)propyl]aminomethyl]phenoxy]butyric acid.

(28) The compound or a salt thereof, or a solvate of the compound, or a solvate of the salt of the compound for use according to (26) or (27), wherein the cholesterol absorption inhibitor is ezetimibe.

(29) The compound or a salt thereof, or a solvate of the compound, or a solvate of the salt of the compound for use according to any one of (26) to (28), wherein a disease in a subject requiring increase of HDL cholesterol (HDL-C) is selected from the group consisting of mixed dyslipidemia, metabolic syndrome, dyslipidemia complicated by diabetes, hypo-HDL cholesterolemia (hypo HDL-C-emia), and hypertriglyceridemia (hyper TG-emia). (30) The compound or a salt thereof, or a solvate of the compound, or a solvate of the salt of the compound for use according to anyone of (26) to (29), wherein an amount ratio of the compound represented by the general formula (1) to the cholesterol absorption inhibitor in the pharmaceutical composition is 1:200 to 3:1.

Effects of the Invention

The agent and pharmaceutical composition of the present invention have an excellent blood HDL cholesterol increasing effect, and are useful in the prevention and/or treatment of dyslipidemia, particularly mixed dyslipidemia, metabolic syndrome, dyslipidemia complicated by diabetes, hypo-HDL cholesterolemia, or hypertriglyceridemia.

MODES FOR CARRYING OUT THE INVENTION

Figure 1:
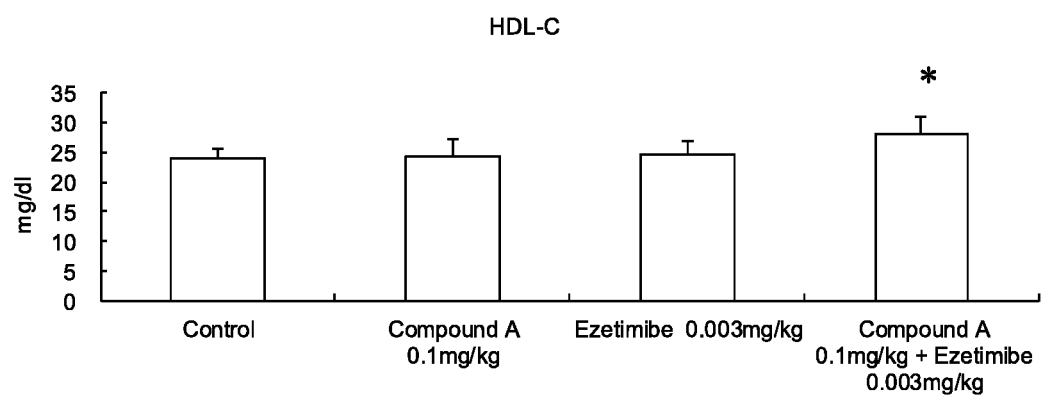
FIG. 1 illustrates plasma HDL-C levels when compound A and ezetimibe are administered each alone or in combination.

Examples of the halogen atom of $R^{3a}$, $R^{3b}$, $R^{4a}$, and $R^{4b}$ in the general formula (1) include a fluorine atom, a chlorine atom, and a bromine atom. Among them, a fluorine atom and a chlorine atom are particularly preferable.

Examples of the C1-4 alkyl group of $R^{3a}$, $R^{3b}$, $R^{4a}$, $R^{4b}$ and $R^5$ include a methyl group, an ethyl group, an n-propyl group, an isopropyl group, and a butyl group. Among them, a methyl group is particularly preferable.

Examples of the $C_{1-4}$ alkoxy group of $R^{3a}$, $R^{3b}$, $R^{4a}$ and $R^{4b}$ include a methoxy group, an ethoxy group, an n-propoxy group, an isopropoxy group, and a butoxy group. Among them, a methoxy group is particularly preferable.

Examples of the $C_{1-4}$ alkylcarbonyloxy group of $R^{3a}$, $R^{3b}$, $R^{4a}$ and $R^{4b}$ include a methylcarbonyloxy group, an ethylcarbonyloxy group, an n-propylcarbonyloxy group, an isopropylcarbonyloxy group, and a butylcarbonyloxy group. Among them, a methylcarbonyloxy group is particularly preferable.

Examples of the di-$C_{1-4}$ alkylamino group of $R^{3a}$, $R^{3b}$, $R^{4a}$ and $R^{4b}$ include a dimethylamino group, a diethylamino group, and a diisopropylamino group. Among them, a dimethylamino group is particularly preferable.

Examples of the $C_{1-4}$ alkylsulfonyloxy group of $R^{3a}$, $R^{3b}$, $R^{4a}$ and $R^{4b}$ include a methylsulfonyloxy group, and an ethylsulfonyloxy group. Among them, a methylsulfonyloxy group is particularly preferable.

Examples of the $C_{1-4}$ alkylsulfonyl group of $R^{3a}$, $R^{3b}$, $R^{4a}$, $R^{4b}$, and $R^5$ include a methylsulfonyl group, and an ethylsulfonyl group. Among them, a methylsulfonyl group is particularly preferable.

Examples of the $C_{1-4}$ alkylsulfinyl group of $R^{3a}$, $R^{3b}$, $R^{4a}$ and $R^{4b}$ include a methylsulfinyl group, and an ethylsulfinyl group. Among them, a methylsulfinyl group is particularly preferable.

Examples of the $C_{1-4}$ alkylthio group of $R^{3a}$, $R^{3b}$, $R^{4a}$ and $R^{4b}$ include a methylthio group, and an ethylthio group. Among them, a methylthio group is particularly preferable.

Examples of the alkylenedioxy group in which $R^{3a}$ and $R^{3b}$, or $R^{4a}$ and $R^{4b}$ are bonded to each other include a methylenedioxy group, and an ethylenedioxy group. Among them, a methylenedioxy group is particularly preferable.

Examples of the $C_{1-4}$alkyloxycarbonyl group of $R^5$ include a methyloxycarbonyl group, and an ethyloxycarbonyl group. Among them, a methyloxycarbonyl group is particularly preferable.

$R^1$ and $R^2$ are particularly preferably hydrogen atoms at the same time, or methyl groups at the same time; or a methyl group and a hydrogen atom, or an ethyl group and a hydrogen atom.

X represents an oxygen atom, a sulfur atom, or N-$R^5$, and is preferably an oxygen atom. Further, Y represents an oxygen atom, a $S(O)_1$ group, a carbonyl group, a carbonylamino group, an aminocarbonyl group, a sulfonylamino group, an aminosulfonyl group, or an NH group, and is preferably an oxygen atom. Z represents CH or N, and is preferably CH. 1 represents 0, 1 or 2, and is preferably 2. n represents a number from 1 to 6, and is preferably from 1 to 3. m represents a number from 2 to 6, is preferably 2 to 4, and is particularly preferably 2 or 3.

Preferable examples of the compound represented by the general formula (1) of the present invention include a compound in which X and Y are oxygen atoms, Z is CH, n is 1, and m is 3. More preferable examples of the compound include a compound in which X and Y are oxygen atoms; Z is CH; n is 1; m is 3; $R^{3a}$ and $R^{3b}$, which may be identical or different, each of which is a hydrogen atom, a halogen atom, a hydroxyl group, a $C_{1-4}$ alkyl group, a trifluoromethyl group, or a $C_{1-4}$ alkoxy group; $R^{4a}$ and $R^{4b}$, which may be identical or different, each of which is a halogen atom, a hydroxyl group, a $C_{1-4}$ alkyl group, a trifluoromethyl group, or a $C_{1-4}$ alkoxy group. More preferable examples of the compound represented by the general formula (1) of the present invention include (R)-2-[3-[[N-(benzoxazol-2-yl)-N-3-(4-methoxyphenoxy)propyl]aminomethyl]phenoxy]butyric acid (hereinafter, may be referred to as "compound A").

Usually, in an amount of around 400 to 500 mg of cholesterol from the diet, and in an amount of around 800 to 2,000 mg of cholesterol from the bile are drawn into the small intestine per day, and around 50% of the cholesterol drawn into the small intestine is absorbed. In the present invention, the cholesterol absorption inhibitor is not particularly limited as long as being able to inhibit the absorption of the cholesterol drawn into the small intestine, and examples of the cholesterol absorption inhibitor include, for example, an anion exchange resin such as cholestyramine, and cholestyramide, and an agent suppressing the absorption of cholesterol by the inhibition of a cholesterol transporter (NPC1-L1), such as ezetimibe, and a compound described in the Patent Documents 11 to 14. Preferable examples of the cholesterol absorption inhibitor of the present invention include, for example, an agent suppressing the absorption of cholesterol by the inhibition of a cholesterol transporter (NPC1-L1), and among them, ezetimibe is more preferable.

A compound represented by the general formula (1) of the present invention can be produced, for example, in accordance with a method described in Patent Document 1.

In addition, in the present invention, a salt or solvate of the compound represented by the general formula (1) can be used. The salt and solvate can be produced by routine procedures.

The salt of the compound represented by the general formula (1) of the present invention is not particularly limited as long as being pharmacologically acceptable, and examples of the salt include, for example, an alkali metal salt such as a sodium salt, and a potassium salt; an alkaline earth metal salt such as a calcium salt, and a magnesium salt; an organic base salt such as an ammonium salt, and a trialkylamine salt; a mineral acid salt such as a hydrochloride, and a sulfate; and an organic acid salt such as an acetate.

Examples of the solvate of the compound represented by the general formula (1) or the salt thereof of the present invention include a hydrate, and an alcohol solvate (for example, an ethanol solvate).

The compound represented by the general formula (1) of the present invention has an asymmetric carbon atom, and therefore has optical isomers of a R-isomer and a S-isomer, and all the optical isomers are included in the present invention.

Ezetimibe (chemical name: (3R,4S)-1-(4-fluorophenyl)-3-{(3S)-3-(4-fluorophenyl)-3-hydroxypropyl}-4-(4-hydroxyphenyl)azetidin-2-one (IUPAC)) can be produced by a method described in J. Org. Chem., 64 (10), 3714-3718 (1999), Tetrahedron Lett., 44(4), 801-804 (2003), and the like. Further, a pharmaceutical product available on the market may be used.

As indicated in Examples below, when a compound represented by the general formula (1) is used in combination with a cholesterol absorption inhibitor, each plasma lipid parameter is improved and particularly a strong HDL-C increasing effect is exerted in an evaluation system using a rat loaded with high cholesterol diet. Therefore, an agent of the present invention is useful in the prevention and/or treatment of mixed dyslipidemia, metabolic syndrome, dyslipidemia complicated by diabetes, hypo-HDL cholesterolemia, or hypertriglyceridemia.

The dyslipidemia in the present invention means that any one or two or more of the total triglyceride (TG) level, the total cholesterol (TC) level, the VLDL cholesterol (VLDL-C) level, the LDL cholesterol (LDL-C) level, or the HDL cholesterol (HDL-C) level, in the blood deviate from a range of the normal level.

In addition, the disease in a subject requiring increase of HDL cholesterol (HDL-C) in the present invention means the case where the HDL-C level in the blood is lower than the normal level.

The compound represented by the general formula (1) or a salt thereof, or a solvate of the compound, or a solvate of the salt of the compound of the present invention can be prepared alone or in combination with other pharmaceutically acceptable carriers, into a dosage form of a tablet, a capsule, granules, powders, lotion, ointment, an injection, a suppository, and the like. These pharmaceutical preparations can be produced by a known method. For example, a preparation for oral administration can be produced by the formulation of a solubilizer such as tragacanth gum, gum arabic, sucrose fatty acid ester, lecithin, olive oil, soybean oil, and PEG 400; an excipient such as starch, mannitol, and lactose; a binder such as methylcellulose, carboxymethylcellulose sodium, and hydroxypropylcellulose; a disintegrant such as crystalline cellulose, and carboxymethylcellulose calcium; a lubricant such as talc, and magnesium stearate; a fluidity-improving agent such as light silicic anhydride; and the like, in appropriate combination.

As to the usage form of the pharmaceutical composition of the present invention, a) a compound represented by the general formula (1) or a salt thereof, or a solvate of the compound, or a solvate of the salt of the compound is used in combination with b) a cholesterol absorption inhibitor, and the pharmaceutical composition can be used in a form in which a prophylactic and/or therapeutic effect for dyslipidemia such as mixed dyslipidemia, metabolic syndrome, dyslipidemia complicated by diabetes, hypo-HDL cholesterolemia, and hypertriglyceridemia is exerted with the use of the synergistic blood HDL-C increasing effect by the administration of both agents in addition to each effect of agents, however, is not limited to these usage forms. The compound represented by the general formula (1) and the cholesterol absorption inhibitor may be administered at the same time, or may be administered separately at intervals.

The compound represented by the general formula (1) and the cholesterol absorption inhibitor may be prepared together into a single preparation, or may be prepared separately into each preparation and used as a kit. That is, the pharmaceutical composition of the present invention may be a kit composed of an agent containing as an active component at least one kind selected from a compound represented by the general formula (1) or a salt thereof, or a solvate of the compound, or a solvate of the salt of the compound, and an agent containing at least one kind of cholesterol absorption inhibitors in combination.

When both agents are administered as a single preparation in the present invention, the mixing ratio of the compound represented by the general formula (1) to the cholesterol absorption inhibitor can be appropriately selected in the range of effective dose of each active component, however, the mixing ratio is generally preferably in the range of 5:1 to 1:30,000 by amount ratio, and more preferably in the range of 5:1 to 1:1,000 by amount ratio. In particular, in a case where the cholesterol absorption inhibitor is an agent such as ezetimibe, which suppresses the absorption of cholesterol by the inhibition of a cholesterol transporter (NPC1-L1), the mixing ratio is preferably in the range of 5:1 to 1:300, and more preferably 3:1 to 1:200 by amount ratio from the viewpoint that the particularly excellent synergistic effect is obtained.

In a case where the compound represented by the general formula (1) and the cholesterol absorption inhibitor are separately prepared, the dosage forms of both preparations may be the same as or different from each other. Further, the number of administrations of each component may vary.

The compound represented by the general formula (1) or a salt thereof, or a solvate of the compound, or a solvate of the salt of the compound of the present invention is orally or parenterally administered. The dosage of the pharmaceutical of the present invention varies depending on the body weight, age, sex, symptoms and the like of a subject, however, usually in a case of an adult human, the dosage of 0.001 to 100 mg, and preferably 0.01 to 10 mg is preferably administered while being divided into 1 to 3 times per day as for the compound of the general formula (1). Further, the cholesterol absorption inhibitor is preferably administered in a dosage of 0.01 to 1,000 mg, and preferably 1 to 100 mg while being divided into 1 to 3 times per day as the ezetimibe.

EXAMPLES

Hereinafter, the present invention will be more specifically explained by way of Examples, Comparative Example, and Preparation Example, however should not be limited at all by these Examples.

Example 1 Combined Effect of Compound A and Ezetimibe for on High-Cholesterol Diet-Fed Rats 1. Procedure SD rats (6 weeks old, male, CHARLES RIVER LABORATORIES JAPAN, INC.) were used in the experiments. Blood was collected from the jugular vein of chow-fed rat, and divided into 4 groups (N=8) base on the levels of TG and TC in the plasma, and the body weight. From the next day, a solid chow containing 2% cholesterol and 0.5% sodium cholate (MF-based, Oriental Yeast Co., Ltd.) was loaded to rats for one week. In parallel to the loading with the high cholesterol diet, a vehicle (an aqueous solution of 0.5% methylcellulose:MC), or (R)-2-[3-[[N-(benzoxazol-2-yl)-N-3-(4-methoxyphenoxy)propyl]aminomethyl]phenoxy]butyric acid (compound A) and/or ezetimibe was orally administered once a day. In the afternoon of the last day of the administration, blood was collected under pentobarbital anesthesia after the fasting period of 4 hours, and the HDL-C levels in the plasma were measured. The synergistic effect was determined by using Burgi's formula (if the relative level in the combined group is larger than the value of the product of the relative level of single agent A and the relative level of single agent B, the synergistic effect is positive).

2. Group Configuration
   Group 1: Control
   Group 2: Compound A 0.1 mg/kg
   Group 3: Ezetimibe 0.003 mg/kg
   Group 4: Compound A 0.1 mg/kg and ezetimibe 0.003 mg/kg 3. Statistical Analysis and Data Processing Method The results were shown as the mean±standard deviation. Comparison between the control group and the drug administration group was performed using Dunnett's multiple comparison test, and the risk rate of less than 5% was determined to have a significant difference.

4. Results

The results are shown in FIG. 1 and Table 1. In addition, the average level of each group of HDL-C is shown in Table 1. In the single administration group of compound A or ezetimibe, apparent effects were not recognized for the HDL-C level. However, in the combined administration group of 0.1 mg/kg of compound A and 0.003 mg/kg of ezetimibe, significant (*: $p<0.05$, to the control) and synergistic (the relative level (1.167) in the combined group is larger than the value of the product ($1.010 \times 1.022 = 1.032$) of the relative level in the single agent A administration group to the control group and the relative level in the single agent B administration group to the control group) increase of HDL-C level was recognized (FIG. 1, and Table 1).

TABLE 1

|  | Control | Compound A 0.1 mg/kg | Ezetimibe 0.003 mg/kg | Compound A 0.1 mg/kg + Ezetimibe 0.003 mg/kg |
|---|---|---|---|---|
| Ave. | 24.1 | 24.3 | 24.6 | 28.1 |
| SD | 1.6 | 3.0 | 2.4 | 2.9 |
| HDL-C Rate of Change | — | 1.0% | 2.2% | 16.7% |

Example 2 Combined Effect of Compound A and Ezetimibe on High-Cholesterol Diet-Fed Rats 1. Procedure SD rats (6 weeks old, male, CHARLES RIVER LABORATORIES JAPAN, INC.) were used in the experiments. Blood was collected from the jugular vein of chow-fed rat, and divided into 6 groups (N=6, 8) base on the levels of TG and TC in the plasma, and the body weight. From the next day, a solid food containing 2% cholesterol and 0.5% sodium cholate (MF-based, Oriental Yeast Co., Ltd.) was loaded to rats for one week. In parallel to the loading with the high cholesterol diet, a vehicle (0.5% MC), or compound A and/or ezetimibe was orally administered once a day. In the afternoon of the last day of the administration, blood was collected under pentobarbital anesthesia after the fasting period of 4 hours, and the TG levels and TC levels in the plasma, and lipid levels in the lipoprotein (VLDL-C, LDL-C and HLDL-C) were measured. The synergistic effect was determined by using Burgi's formula (in a case where a level lower than that in the control group is indicated in a drug administration group, that is, when the evaluation of an agent to the TC, VLDL-C, or LDL-C is performed, if the relative level in the combined group is smaller than the value of the product of the relative level of single agent A and the relative level of single agent B, the synergistic effect exists. In a case where a level higher than that in the control group is indicated in a drug administration group, that is, when the evaluation of an agent to the HDL-C is performed, if the relative level in the combined group is larger than the value of the product of the relative level of single agent A and the relative level of single agent B, the synergistic effect exists).

2. Group Configuration
   Group 1: Control
   Group 2: Compound A 0.1 mg/kg
   Group 3: Ezetimibe 0.01 mg/kg
   Group 4: Combination of compound A 0.1 mg/kg and ezetimibe 0.01 mg/kg
   Group 5: Ezetimibe 0.1 mg/kg
   Group 6: Combination of compound A 0.1 mg/kg and ezetimibe 0.1 mg/kg 3. Statistical Analysis and Data Processing Method The results were shown as the mean±standard deviation. Comparison between the control group and the drug administration group was performed using Dunnett's multiple comparison test, and the risk rate of less than 5% was determined to have a significant difference.

4. Results

Figure 2:
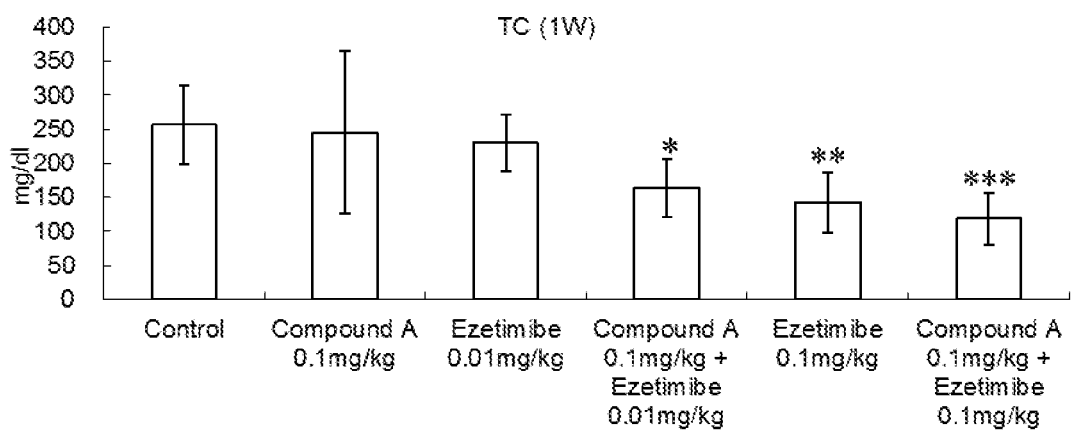
FIG. 2 illustrates plasma TC levels when compound A and ezetimibe are administered each alone or in combination.
Figure 3:
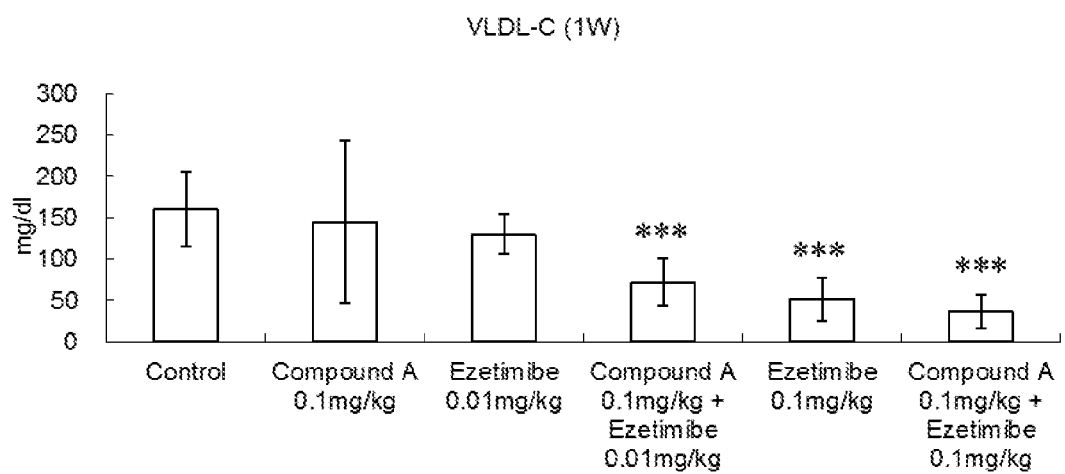
FIG. 3 illustrates plasma VLDL-C levels when compound A and ezetimibe are administered each alone or in combination.
Figure 4:
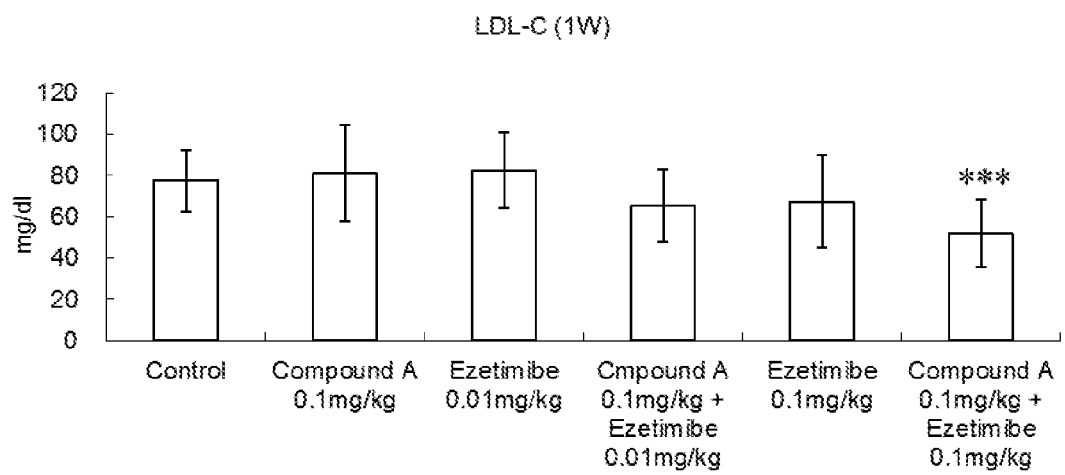
FIG. 4 illustrates plasma LDL-C levels when compound A and ezetimibe are administered each alone or in combination.
Figure 5:
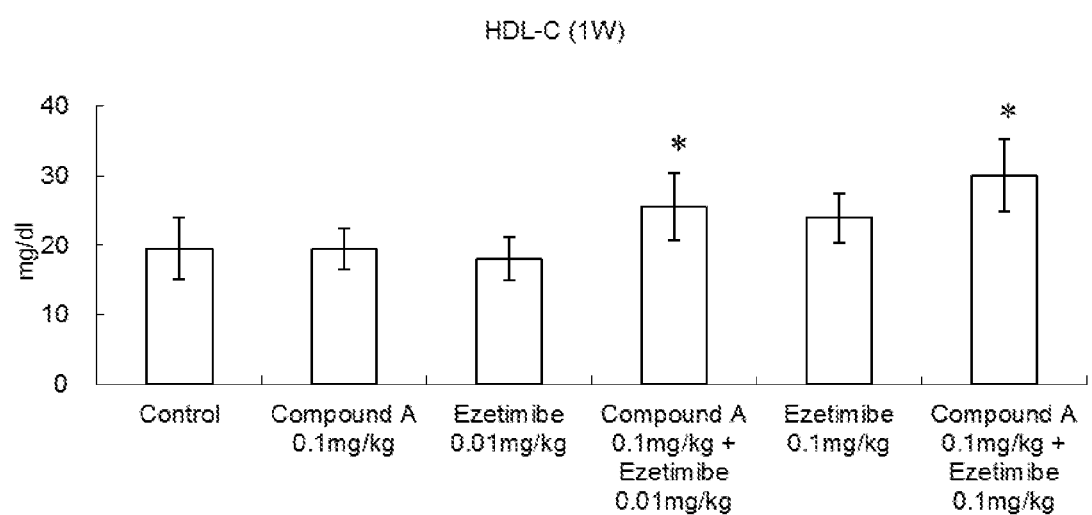
FIG. 5 illustrates plasma HDL-C levels when compound A and ezetimibe are administered each alone or in combination.

The results are shown in Table 2 and FIGS. 2 to 5. FIG. 2 shows the results of the total cholesterol (TC) levels, FIG. 3 shows the VLDL cholesterol (VLDL-C) levels, FIG. 4 shows the LDL cholesterol (LDL-C) levels, and FIG. 5 shows the HDL cholesterol (HDL-C) levels. The symbol in FIGS. means as follows: *: $p<0.05$, : $p<0.01$, and *: $p<0.001$.

Synergistic Effects by the Combination of Compound A with Ezetimibe on the High-Cholesterol Diet-Fed Rats

TABLE 2

| Compound A (mg/kg) | | 0.1 | — | 0.1 | — | 0.1 |
|---|---|---|---|---|---|---|
| Ezetimibe (mg/kg) | | — | 0.01 | 0.01 | 0.1 | 0.1 |
| TC | Relative Level (to Control) | 0.956 | 0.898 | 0.635 | 0.555 | 0.462 |
|  | Bürgi's Formula |  |  | 0.859 |  | 0.530 |
| VLDL-C | Relative Level (to Control) | 0.827 | 0.719 | 0.374 | 0.262 | 0.179 |
|  | Bürgi's Formula |  |  | 0.595 |  | 0.217 |
| LDL-C | Relative Level (to Control) | 0.971 | 0.955 | 0.713 | 0.720 | 0.529 |
|  | Bürgi's Formula |  |  | 0.927 |  | 0.698 |
| HDL-C | Relative Level (to Control) | 1.021 | 0.910 | 1.204 | 1.100 | 1.326 |
|  | Bürgi's Formula |  |  | 0.929 |  | 1.123 |

As to each numerical value, the value in the upper shows a relative level to the control group, and the value in the lower shows the product of the relative levels in the compound A single administration group and the ezetimibe single administration group by using Burgi's formula. The values in the underlined part show that the synergistic effect is recognized.

Firstly, when the attention was focused on TC (Table 2 and FIG. 2), the relative level of the compound A single administration group was 0.956, the relative level of the 0.01 mg/kg single administration group of ezetimibe was 0.898, and the product of both relative levels was 0.859. On the other hand, the relative level of the combined administration group of compound A and 0.01 mg/kg of ezetimibe was 0.635, and was significantly decreased as compared with the product of levels in the single administration groups, therefore, the synergistic TC lowering effect was confirmed.

Further, the relative level of 0.1 mg/kg single administration group of ezetimibe was 0.555, and the product of the relative level 0.555 and the relative level 0.956 of the compound A administration group was 0.530, whereas the relative level of 0.1 mg/kg combined administration group of the compound A and the ezetimibe was 0.462, therefore, it was revealed that the synergistic TC lowering effect was recognized also in the high-dose group of ezetimibe.

In the same manner, by the combined administration of the compound A and the ezetimibe, the synergistic lowering effect for the VLDL-C level and LDL-C level, and the synergistic increasing effect for the HDL-C level were recognized.

Comparative Example Combined Effect of Fenofibrate and Ezetimibe on High-Cholesterol Diet-Fed Rats 1. Procedure SD rats (6 weeks old, male, CHARLES RIVER LABORATORIES JAPAN, INC.) were used in the experiments. Blood was collected from the jugular vein of chow-fed rat, and divided into 4 groups (N=8) base on the levels of TG and TC in the plasma, and the body weight. From the next day, a solid chow containing 2% cholesterol and 0.5% sodium cholate (MF-based, Oriental Yeast Co., Ltd.) was loaded to rats for one week. In parallel to the loading with the high cholesterol diet, a vehicle (0.5% MC), or fenofibrate (FF) and/or ezetimibe (Ezeti) was orally administered once a day. In the afternoon of the last day of the administration, blood was collected under pentobarbital anesthesia after the fasting period of 4 hours. The HDL-C levels in the plasma were measured.

2. Group Configuration

Group 1: Control
Group 2: Fenofibrate 10 mg/kg
Group 3: Ezetimibe 0.1 mg/kg
Group 4: Combination of fenofibrate 10 mg/kg and ezetimibe 0.1 mg/kg 3. Statistical Analysis and Data Processing Method The results were shown as the average level±standard deviation. Comparison between the control group and the drug administration group was performed using Dunnett's multiple comparison test, and the risk rate of less than 5% was determined to have a significant difference.

4. Results

Figure 6:
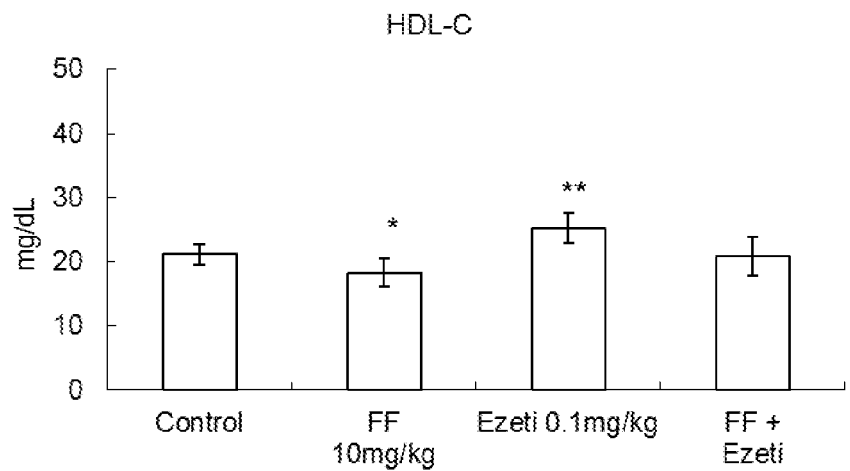
FIG. 6 illustrates plasma HDL-C levels when fenofibrate and ezetimibe are administered each alone or in combination.

The results are shown in FIG. 6. Fenofibrate has also been known as a PPARα agonist, however, the synergistic increasing effect for the HDL-C level was not recognized in the combination of fenofibrate with ezetimibe.

Preparation Example Tablets for Administration Containing Compound A and Ezetimibe The tablets for administration, in which compound A and ezetimibe are contained, can be produced as in the following.

TABLE 3

| Component | Dosage |
| --- | --- |
| Compound A | 0.05 mg |
| Ezetimibe | 10 mg |
| Microcrystalline Cellulose | 37.25 mg |
| Modified food Grade Cornstarch | 37.25 mg |
| Magnesium Stearate | 0.5 mg |

All of the compound A and ezetimibe (amount ratio 1:200) and part of the cellulose and cornstarch were mixed, and the mixture was granulated, as a result, 10% cornstarch paste was obtained. The obtained granules were sieved and dried, and the dried granules were mixed with the remaining part of the cornstarch, and the magnesium stearate. Next, the obtained granules were compressed into a tablet containing 0.05 mg of compound A and 10 mg of ezetimibe per tablet.

INDUSTRIAL APPLICABILITY

The agent and pharmaceutical composition of the present invention have an excellent blood HDL cholesterol increasing effect, and are useful in the prevention and/or treatment of dyslipidemia, particularly mixed dyslipidemia, metabolic syndrome, dyslipidemia complicated by diabetes, hypo-HDL cholesterolemia, or hypertriglyceridemia, therefore have industrial applicability.

The invention claimed is:

1. A method of treating dyslipidemia in a human patient in need thereof comprising administering to said patient a therapeutically effective amounts of (R)-2-[3[[N-benzoxazol-2-yl)-N-3-(4-methoxyphenoxy)propyl]aminomethyl] phenoxy]butyric acid or a pharmaceutically acceptable salt thereof and ezetimibe, wherein said (R)-2-[3-[[N-(benzoxazol-2-yl)-N-3-(4-methoxyphenoxy)propyl]aminomethyl] phenoxy]butyric acid or said pharmaceutically acceptable salt thereof and said ezetimibe are administered to the human patient at the same time or one to three times per day separately at intervals.

2. The method according to claim 1, wherein said (R)-2-[3-[[N-(benzoxazol-2-yl)-N-3-(4-methoxyphenoxy)propyl] aminomethyl]phenoxy]butyric acid or said pharmaceutically acceptable salt therof and said ezetimibe are administered one to three times per day to the human patient seperately at intervals.

3. The method according to claim 1, wherein said patient is suffering from metabolic syndrome.

4. The method according to claim 1, wherein said patient is suffering from diabetes.

5. The method according to claim 1, wherein said patient is suffering from hypo-HDL cholesterolemia.

6. The method according to claim 1, wherein said patient is suffering from hypertriglyceridemia.

7. The method according to claim 1, wherein said patient is suffering from an elevated total triglyceride level and a low HDL cholesterol level.

8. The method according to claim 1, wherein an amount ratio of(R)-2-[3-[[N-(benzoxazol-2-yl)-N-3-(4-methoxyphenoxy)propyl]aminomethyl]phenoxy]butyric acid or a pharmaceutically acceptable salt thereof to ezetimibe is 1:200 to 3:1.

* * * * *